US005383352A

United States Patent [19]
Krawetz et al.

[11] Patent Number: 5,383,352
[45] Date of Patent: Jan. 24, 1995

[54] METHOD FOR THE MEASUREMENT OF BULK MODULUS AND PRESSURE VISCOSITY OF LIQUIDS

[75] Inventors: Arthur A. Krawetz, Evanston; Pricha Klinsuttho, Darien; Phat A. Phan, Skokie, all of Ill.; Quyet Phung, Orange, Calif.

[73] Assignee: The United States of America as represented by the Secretary of the Air Force, Washington, D.C.

[21] Appl. No.: 188,169

[22] Filed: Jan. 26, 1994

[51] Int. Cl.⁶ .................. G01N 33/28; G01N 11/04
[52] U.S. Cl. .................. 73/54.01; 73/53.01; 73/54.06; 73/54.14
[58] Field of Search ............ 73/53.01, 54.01, 54.06, 73/54.14

[56] References Cited
U.S. PATENT DOCUMENTS

| | | | |
|---|---|---|---|
| 1,958,878 | 5/1934 | Albersheim et al. | 73/54.06 |
| 1,963,011 | 6/1934 | Albertsheim et al. | 73/54.06 |
| 2,035,951 | 4/1936 | Eckstein | 73/54.06 |
| 3,302,451 | 2/1967 | Martin | 73/54.06 |
| 3,720,098 | 3/1973 | Dixon | 73/67.7 |
| 3,977,234 | 8/1976 | Lynch et al. | 73/54.06 |
| 4,113,384 | 9/1978 | Lauer et al. | 356/70 |
| 4,193,291 | 3/1980 | Lynnworth | 73/32 A |
| 4,384,472 | 5/1983 | Tournier | 73/54.06 |
| 4,559,810 | 12/1985 | Hinrichs et al. | 73/54 |
| 5,257,529 | 11/1993 | Taniguchi et al. | 73/54.14 |

FOREIGN PATENT DOCUMENTS

| | | | |
|---|---|---|---|
| 1571466 | 6/1990 | U.S.S.R. | 73/54.06 |

*Primary Examiner*—Thomas P. Noland
*Assistant Examiner*—J. David Wiggins
*Attorney, Agent, or Firm*—Donald J. Singer; Irwin P. Garfinkle

[57] ABSTRACT

A method is disclosed for determining bulk modulus of a liquid based on a pressure-volume-temperature relationship at constant volume corrected for changes in system volume due to elevated pressure and temperature. The apparatus used to determine bulk modulus comprises a pressure vessel in which the liquid to be tested is introduced, and from which all gases are removed. The vessel is placed in a constant temperature oven and the pressure is recorded. The method for determining bulk modulus and density requires calibration of the vessel volume changs due to pressure and temperature. The method for determining isothermal bulk modulus requires the solution of an empirical equation:

$$B_i = -\frac{\Delta P \cdot W_{T,P} \cdot v_T}{v_T \cdot (W_T - W_{T,P}) + W_T \cdot \Delta v_{T,P}^{cor}}$$

5 Claims, 10 Drawing Sheets

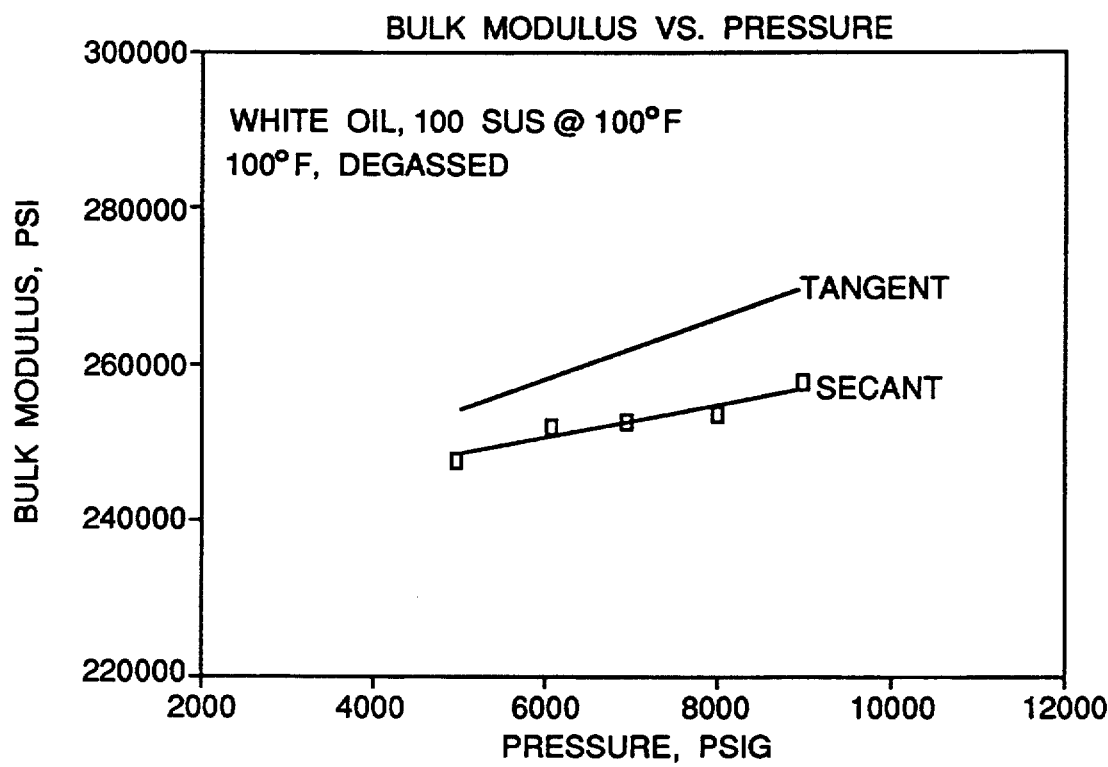
FIG. 3    WHITE OIL, 100 SUS @ 100°F,
BULK MODULUS VS. PRESSURE AT 100°F.
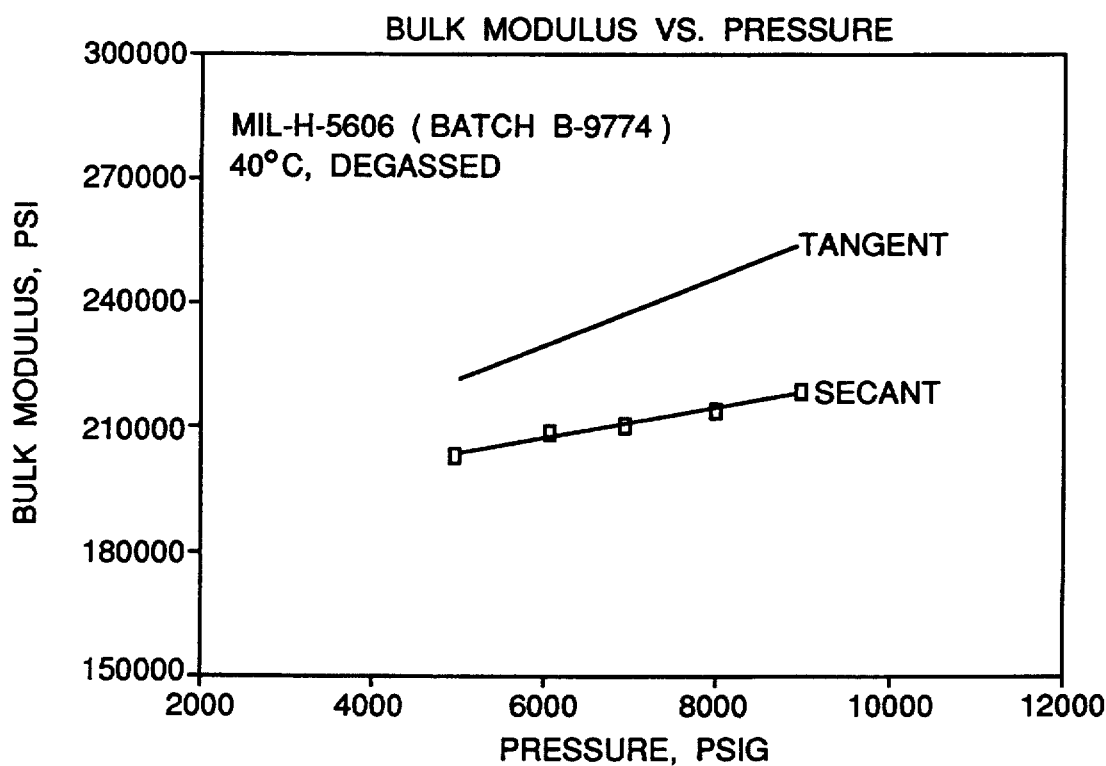
FIG. 4    MIL-H-5606 (BATCH B-9774).
BULK MODULUS VS. PRESSURE AT 40°C.

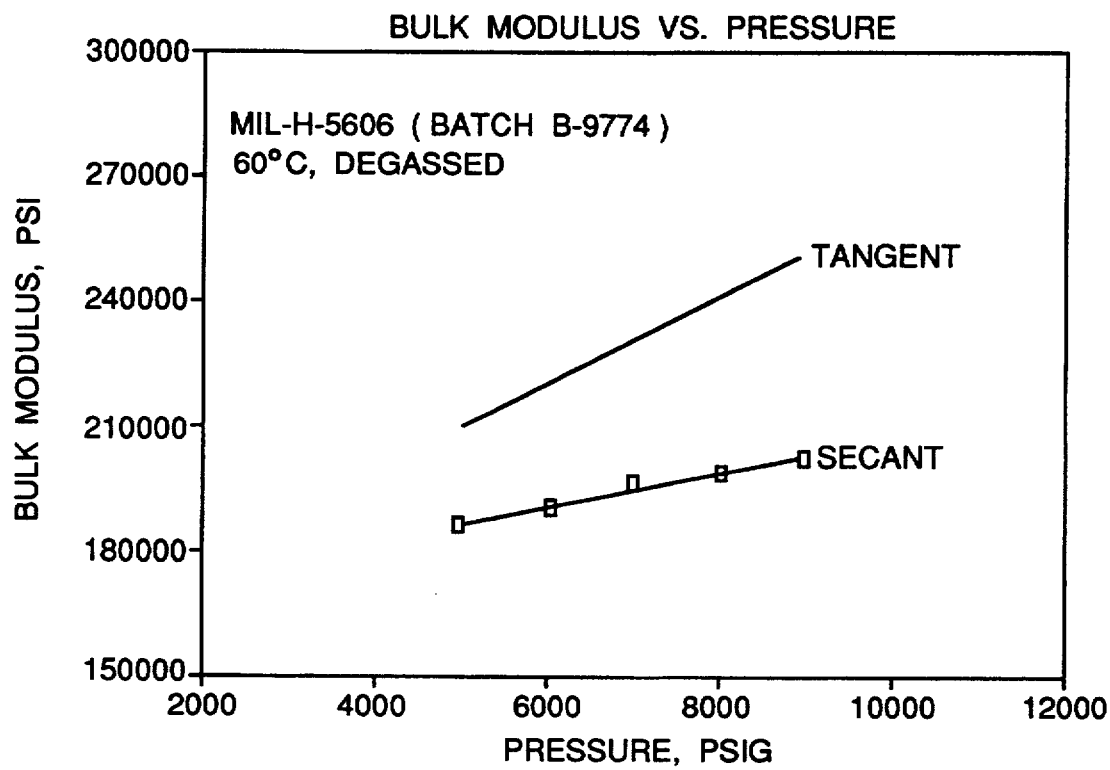
FIG. 5  MIL-H-5606 (BATCH B-9774).
BULK MODULUS VS. PRESSURE AT 60°C.
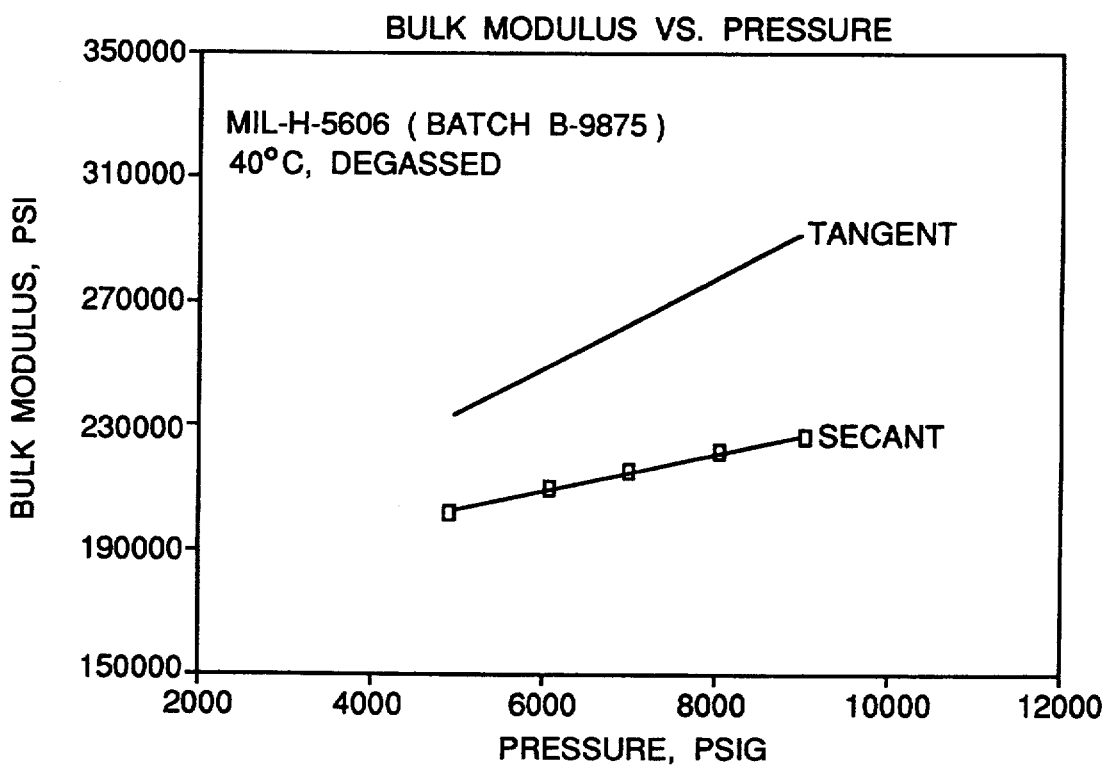
FIG. 6  MIL-H-5606 (BATCH B-9875).
BULK MODULUS VS. PRESSURE AT 40°C.

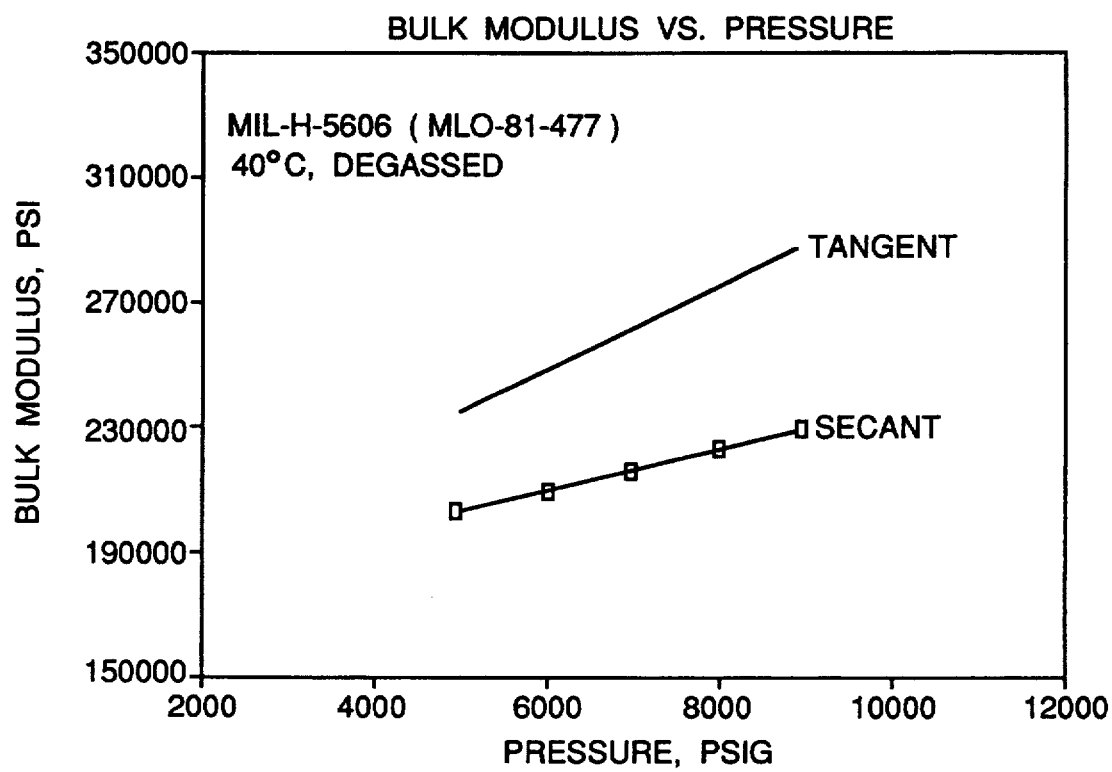
FIG. 7  MIL-H-5606 (MLO-81-477).
BULK MODULUS VS. PRESSURE AT 40°C.
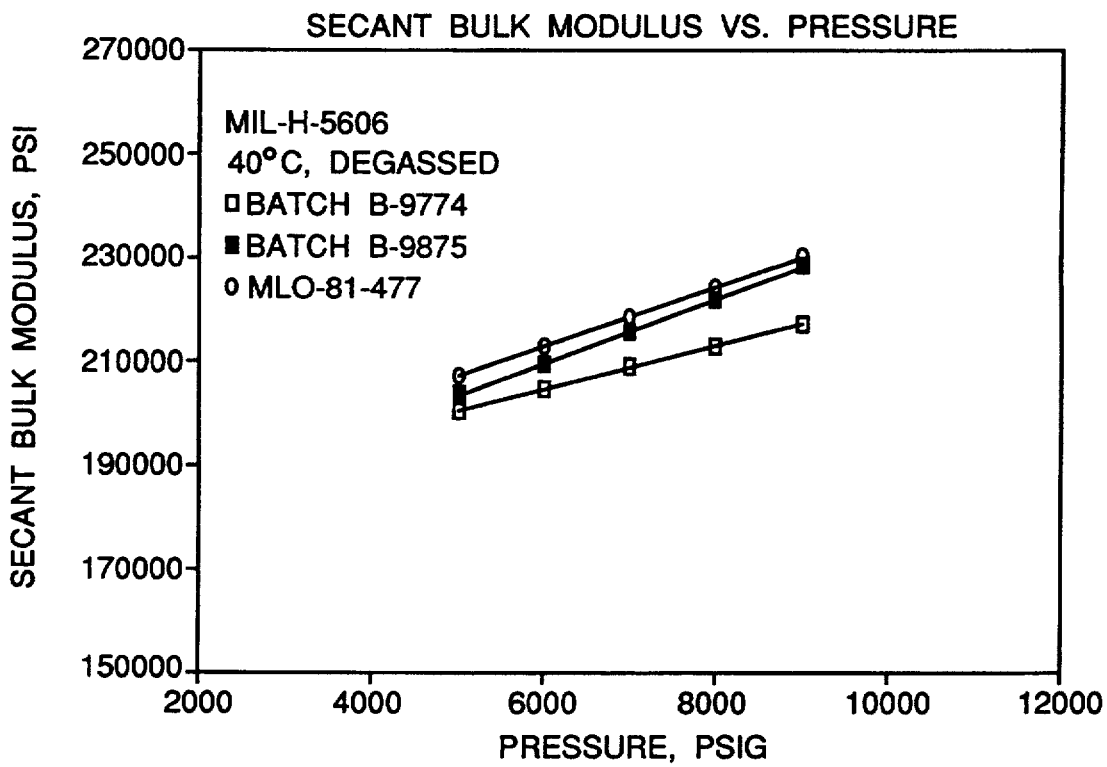
FIG. 8  MIL-H-5606, BATCH B-9774, BATCH 9875 AND MIL-81-477:
SECANT BULK MODULUS VS. PRESSURE.

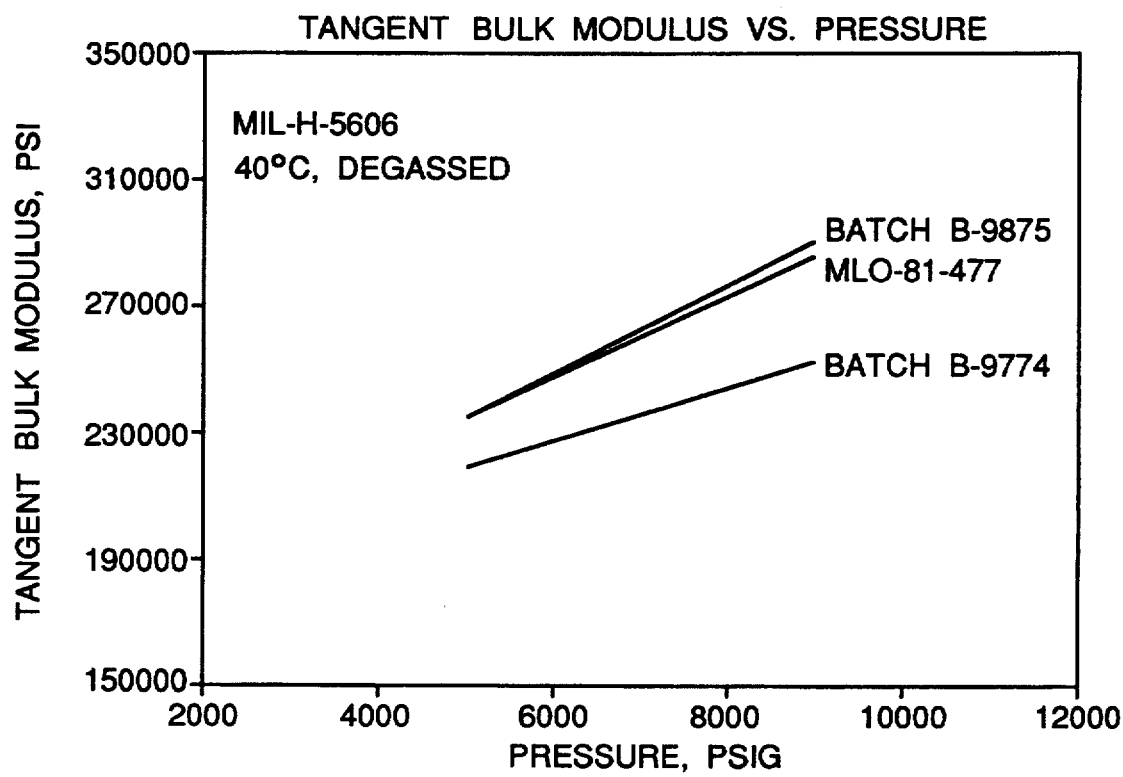
FIG. 9  MIL-H-5606, BATCH B-9774, BATCH 9875 AND MLO-81-477: TANGENT BULK MODULUS VS. PRESSURE.
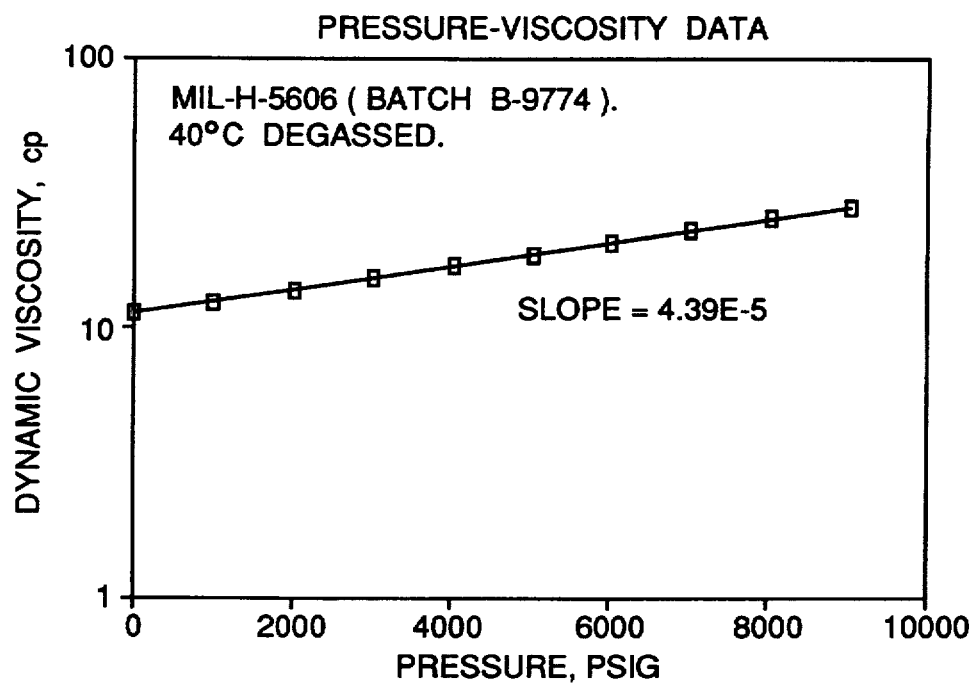
FIG. 10  MIL-H-5606 (BATCH B-9774). DYNAMIC VISCOSITY AT 40°C VS. PRESSURE.

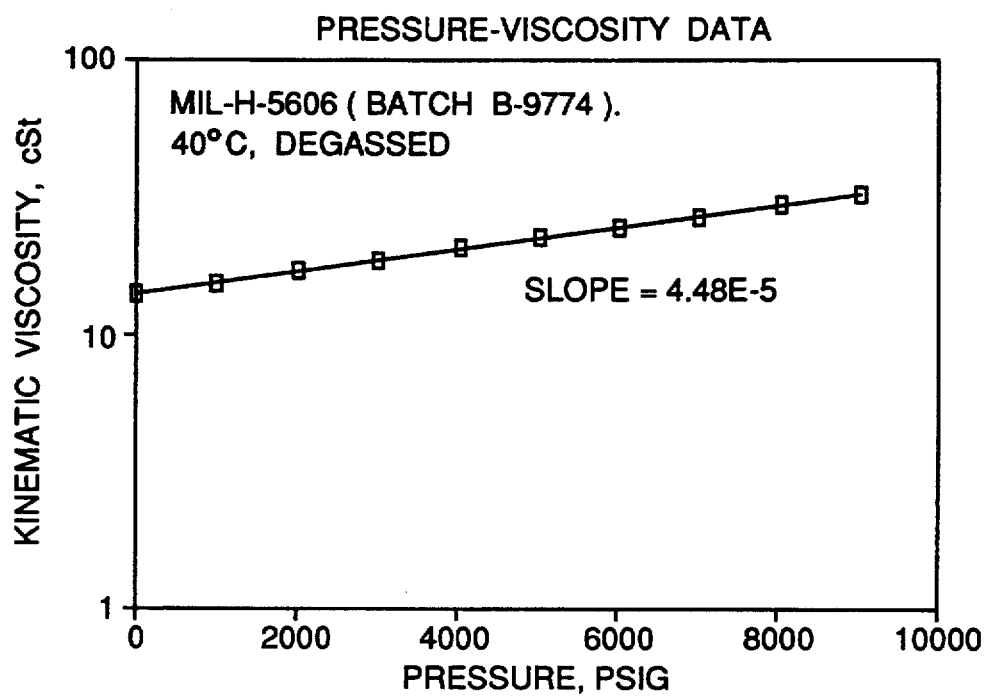
FIG. 11  MIL-L-5606 ( BATCH B-9774 ).
KINEMATIC VISCOSITY AT 40°C VS. PRESSURE.
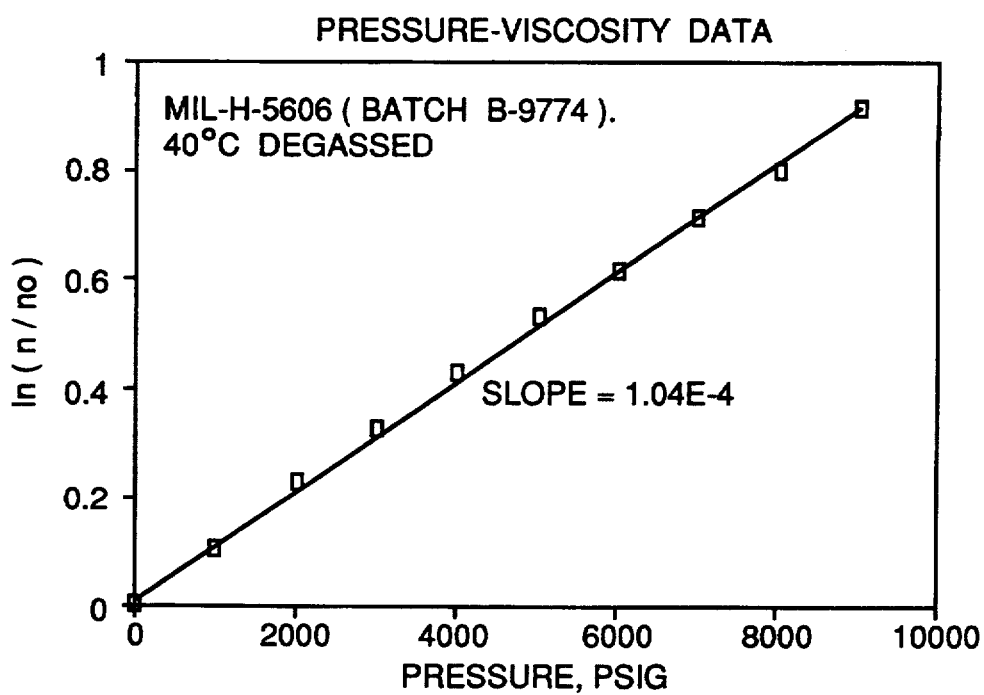
FIG. 12  MIL-H-5606 ( BATCH B-9774 ).
PRESSURE VISCOSITY DATA AT 40°C.

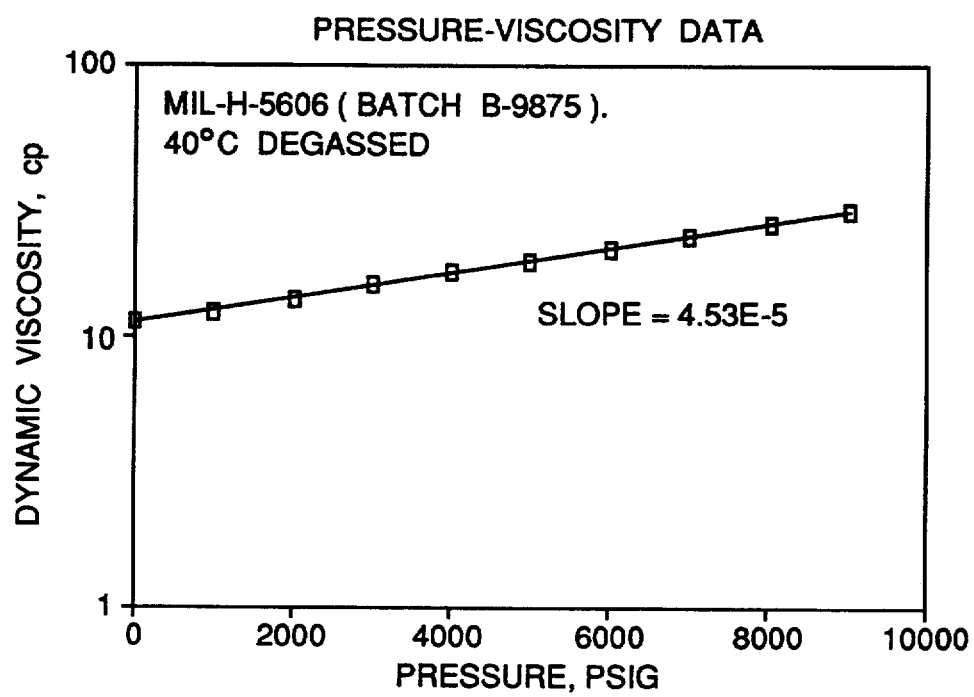
FIG. 13  MIL-H-5606 ( BATCH B-9875 ).
DYNAMIC VISCOSITY AT 40°C VS. PRESSURE.
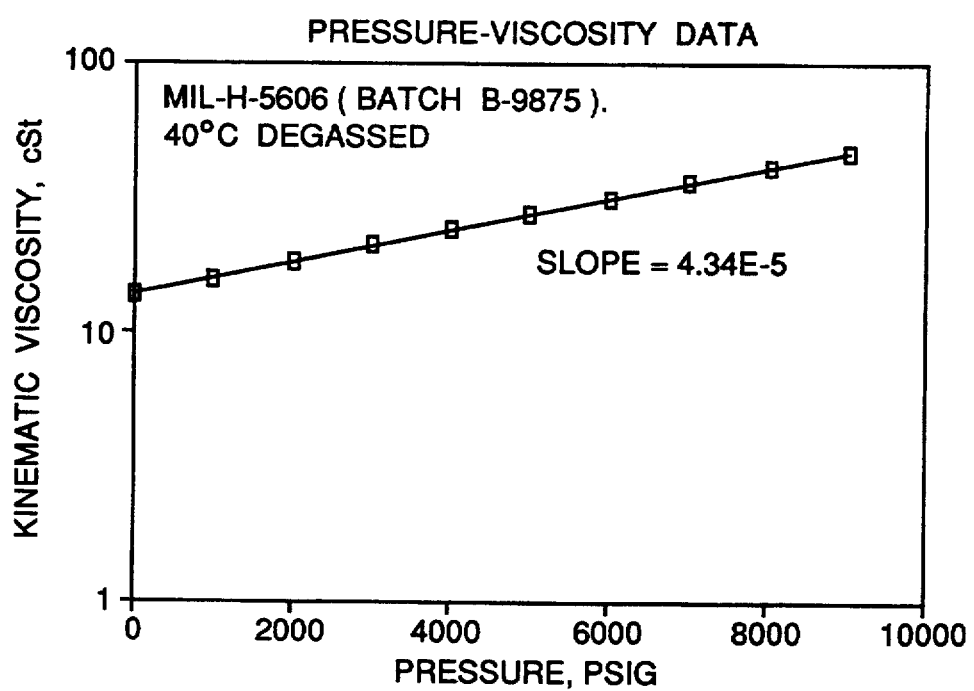
FIG. 14  MIL-H-5606 ( BATCH B-9875 ).
KINEMATIC VISCOSITY AT 40°C VS. PRESSURE.

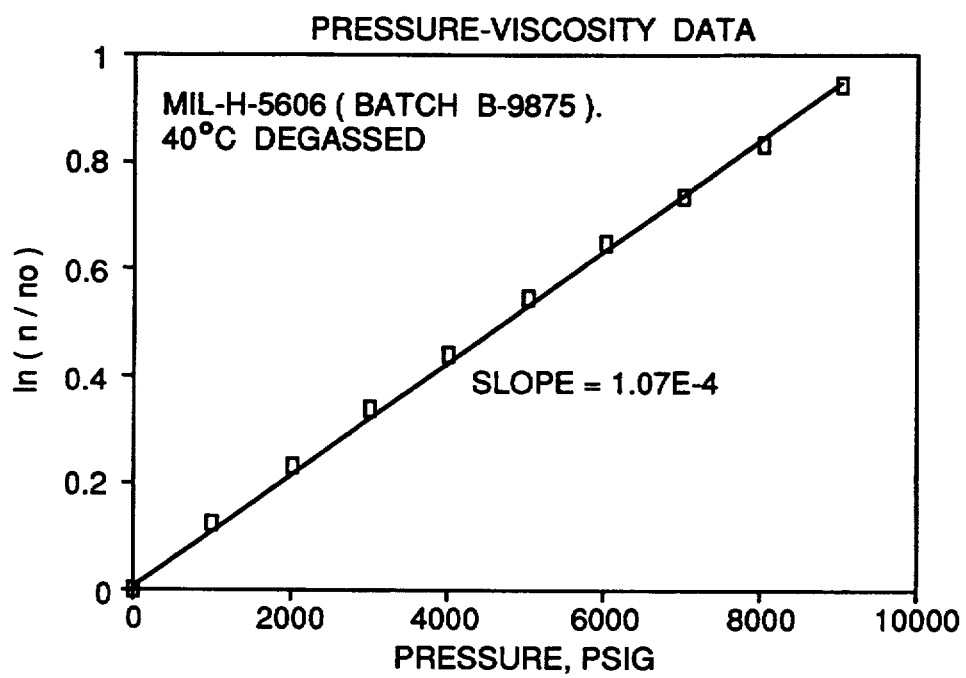
FIG. 15  MIL-H-5606 (BATCH B-9875).
PRESSURE VISCOSITY DATA AT 40°C.
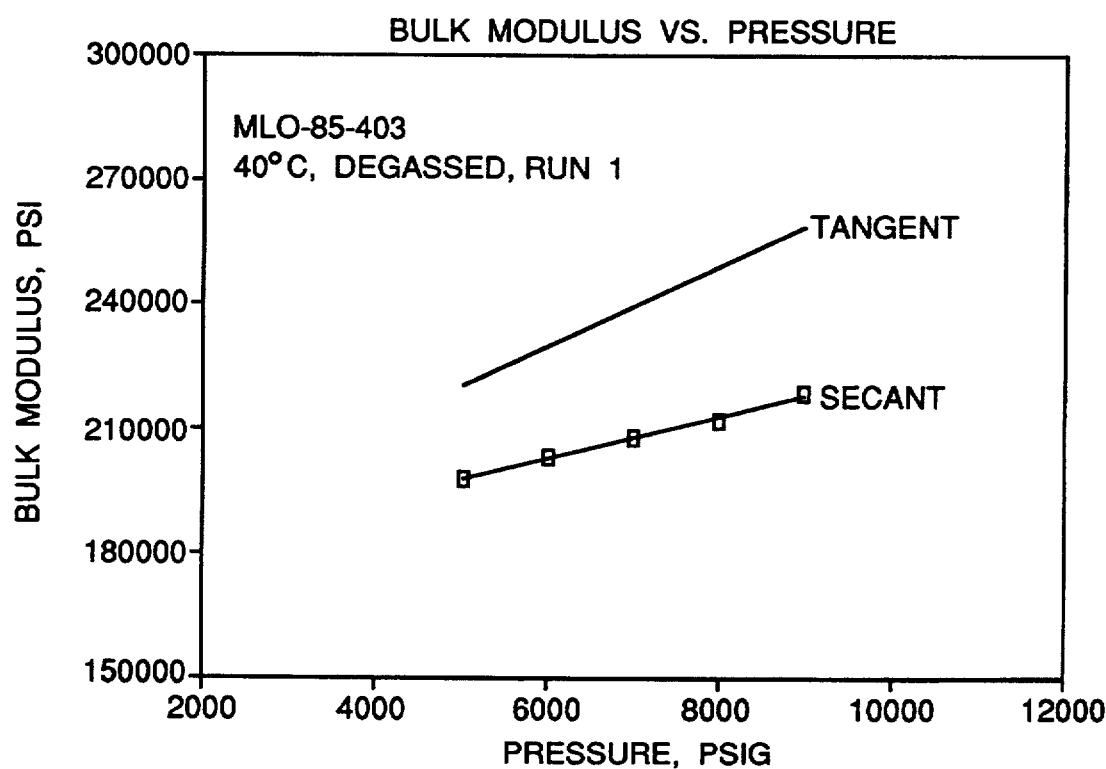
FIG. 16  MIL-85-403.
BULK MODULUS VS. PRESSURE AT 40C° (RUN 1).

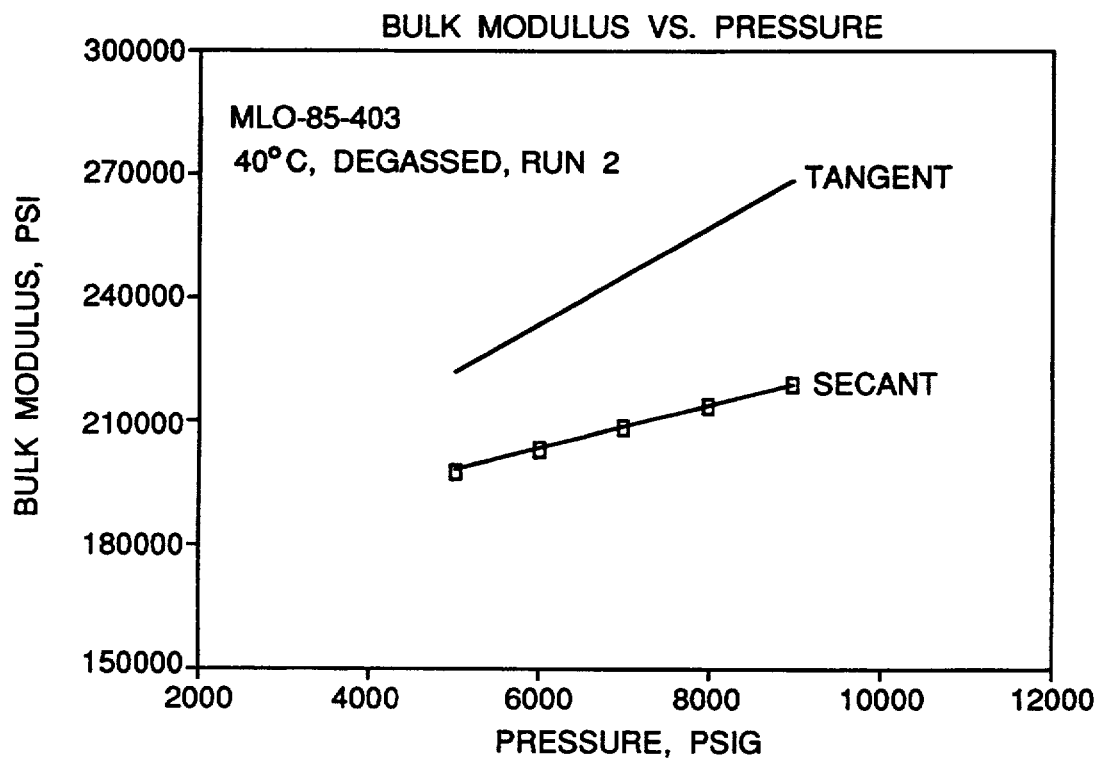
FIG. 17  MLO-85-403.
BULK MODULUS VS. PRESSURE AT 40°C (RUN 2).
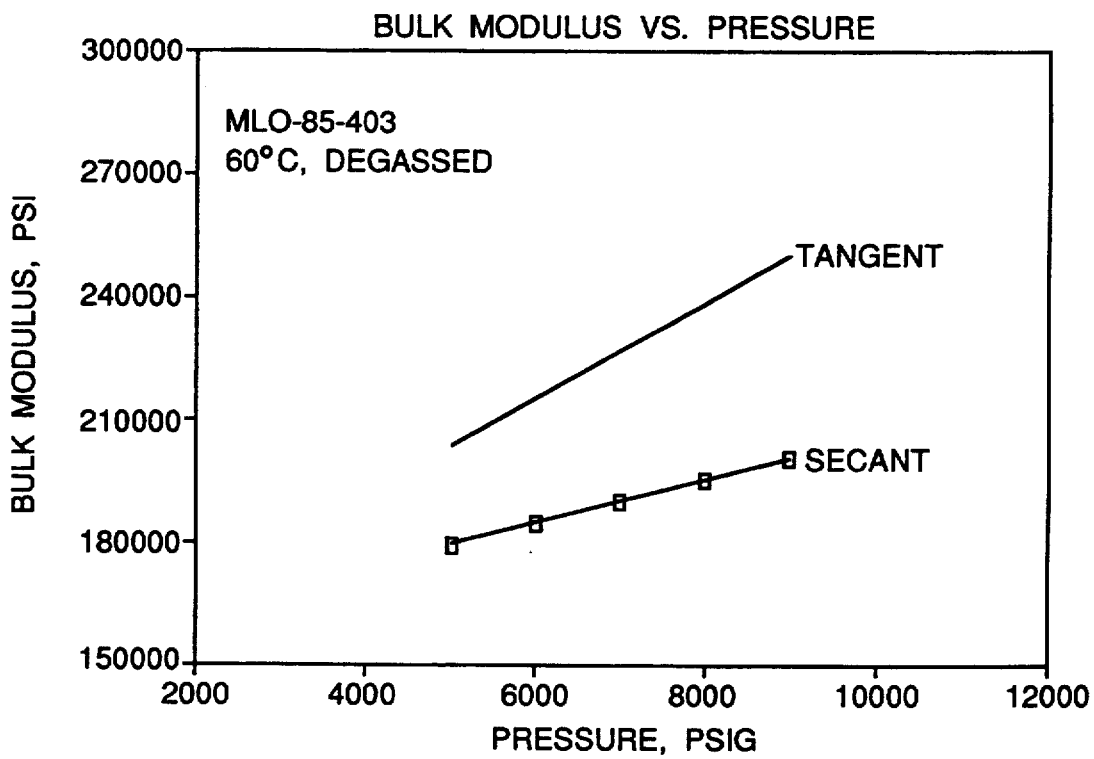
FIG. 18  MLO-85-403.
BULK MODULUS VS. PRESSURE AT 60°C.

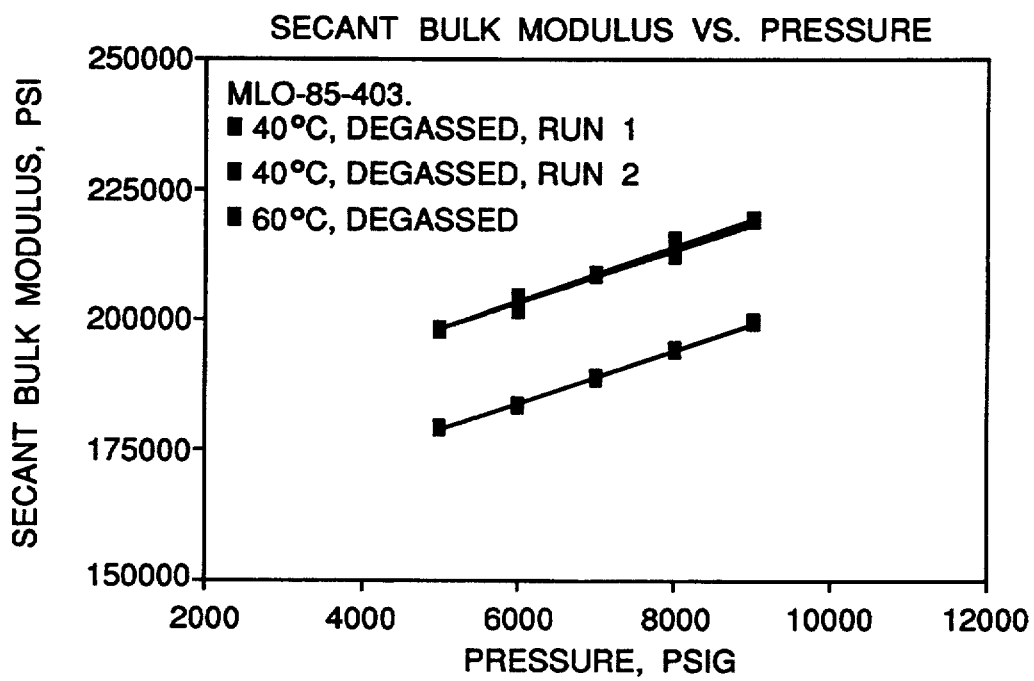
FIG. 19  MLO-85-403. SECANT BULK MODULUS SUMMARY.
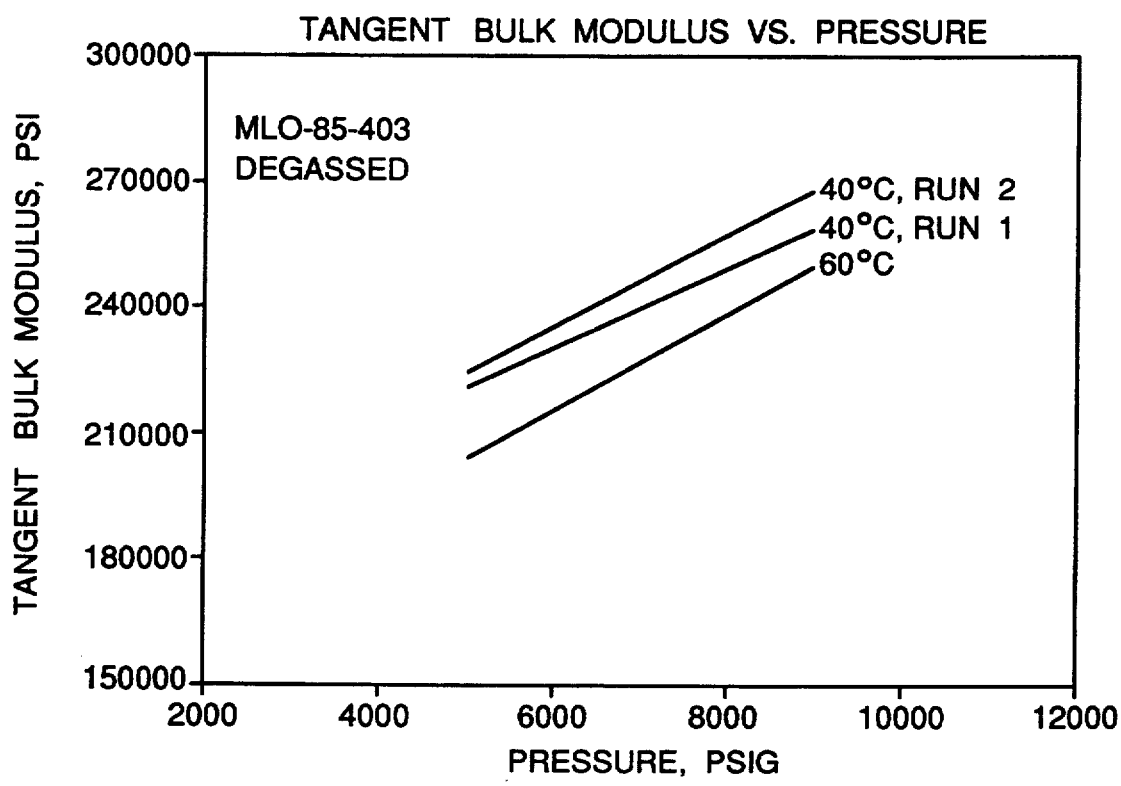
FIG. 20  MLO-85-403. TANGENT BULK MODULUS SUMMARY.

METHOD FOR THE MEASUREMENT OF BULK MODULUS AND PRESSURE VISCOSITY OF LIQUIDS

STATEMENT OF GOVERNMENT INTEREST

The invention described herein may be manufactured and used by or for the Government for governmental purposes without the payment of any royalty thereon.

BACKGROUND OF THE INVENTION

The hydraulic systems required by modern aircraft and missile systems operate at temperatures and pressures which have become increasingly more elevated in response to the demands for increased performance. As a result, the need for the determination of physical properties at high pressures and temperatures has become a requirement of critical proportions. Specific needs include measurement of density, tangent bulk modulus, secant bulk modulus and viscosity at pressures up to 10,000 psia.

SUMMARY OF THE INVENTION

This invention is for a method for the measurement of bulk modulus and pressure viscosity of liquid. The method is based on a pressure-volume-temperature relationship at a constant volume. The apparatus comprises a constant temperature oven, a container vessel within the oven, a plurality of valves, a pump, a regulator and a viscometer. The apparatus is used to obtain a relationship expressing vessel volume at any specified temperature and pressure. This relationship is then used to determine bulk modulus and pressure viscosity.

The invention, together with its advantages, objects and features will become more apparent after considering the following description taken in conjunction with the illustrative embodiments in the accompanying drawings, in which:

BRIEF DESCRIPTION OF THE DRAWINGS

FIGS. 3 through 20 are curves showing samples of the data which were obtained.

DESCRIPTION OF THE PREFERRED EMBODIMENTS

Before discussing the preferred method of the invention, the following are definitions of the terms used herein:

Bulk modulus expresses the resistance of a fluid to compression and can be defined as the reciprocal of compressibility. This property can be determined by both static and dynamic methods. In either case, bulk modulus may be reported as the secant or tangent bulk modulus.

Secant bulk modulus (mean bulk modulus) is defined as a product of the original fluid volume and the slope of the secant drawn from the origin to any specified point on the P vs. $\Delta V/V$ curve.

Isothermal (static) secant bulk modulus is defined as:

$$B_i = -\left[ V_T \frac{\Delta P}{\Delta V} \right]_T \quad (1)$$

where $V_T$ is the volume at T and atm. of the amount of liquid inside the vessel at temperature T and pressure P after being corrected for pressure expansion of the test vessel.

Adiabatic (dynamic or isentropic) secant bulk modulus is defined as:

$$B_a = -\left[ V_T \frac{\Delta P}{\Delta V} \right]_S \quad (2)$$

Tangent bulk modulus is defined as the product of fluid volume at specified pressure and the partial derivative of fluid pressure with respect to volume.

Isothermal (static) tangent bulk modulus is defined as:

$$B_i = -\left[ V^f_{T,P} \frac{\Delta P}{\Delta V} \right]_T \quad (3)$$

where $V^f_{T,P}$ is the volume of liquid at temperature T, obtained from the vessel volume calibration curve.

Adiabatic (dynamic or isentropic) tangent bulk modulus is defined as:

$$B_a = -\left[ V^f_{T,P} \frac{\Delta P}{\Delta V} \right]_S \quad (4)$$

Figure 1:
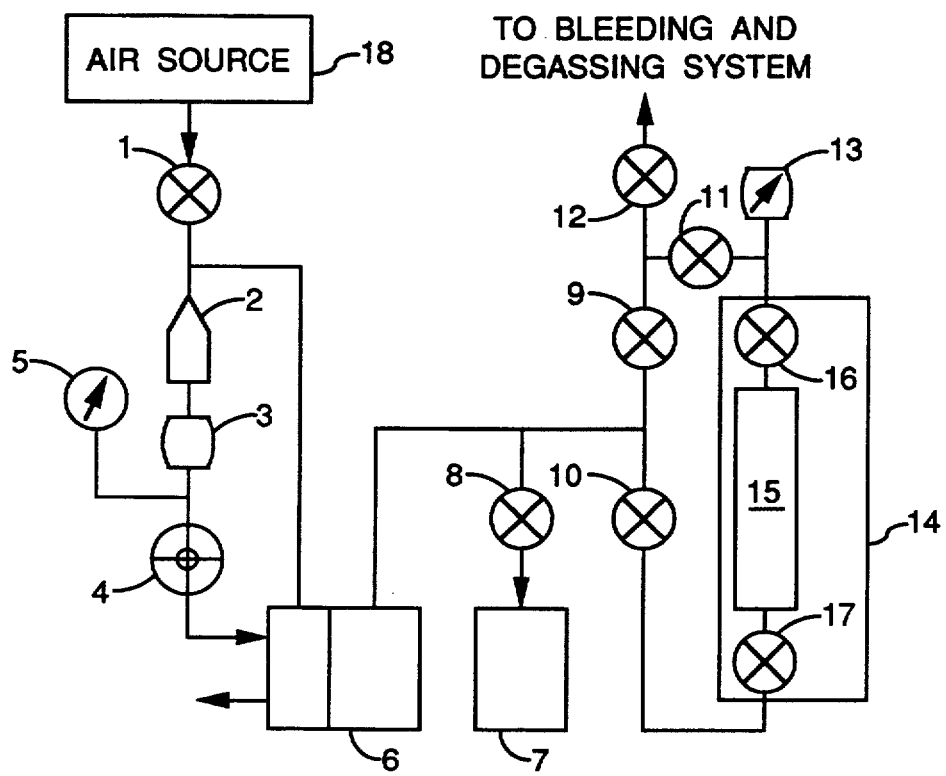
FIG. 1 is a schematic of the Apparatus for the determination of Bulk Modulus and Density at elevated pressure.

The system provided in accordance with this invention is designed to measure bulk modulus of a liquid and is based on a P-V-T relationship at constant volume corrected for changes in system volume due to elevated pressure and temperature As shown in FIG. 1, the apparatus used to determine bulk modulus comprises a pressure vessel 15 in which the liquid to be tested is introduced from a tank 7 through a release valve 8, a pressure balancing valve 9 isolating valves 10 and 11, and vessel valves 16 and 17. The vessel 15, along with the valves 16 and 17 are placed in a constant temperature oven 14. The valve 12 is a bleeding valve. A transducer 13 records the pressure within the vessel 15.

The liquid in vessel 15 is pressurized by means of an air driven liquid pump 6 which is supplied with air from an air source 18 through an air valve 1, an air filter 2, a pressure regulator 3, and a speed control valve 4. The air pressure is monitored by a pressure guage 5.

The method for determining bulk modulus and density requires calibration of the vessel 15. As hereinafter described, the volume of pressure vessel 15 is calibrated at atmospheric pressure and various elevated temperatures to determine the final volume of liquid at any specified temperature and pressure.

Isothermal secant bulk modulus of a liquid is defined as follows:

$$B_i = -\frac{\Delta P}{\frac{V^f_{T,P} - V_T^i}{V_T^i}} \quad (5)$$

where:

$V_{T,P}^f$ is Volume of liquid at T, obtained from the vessel volume calibration curve.

$$v_{T,P}^f = v_T = \frac{W_T}{\rho_T} \qquad (6)$$

$v_T$: Volume of vessel at atmospheric pressure and temperature T.
$W_T$: Weight of liquid at T and 1 atm.
$\rho_T$: Density of liquid at T and 1 atm.
$W_T$ and $\rho_T$ can be obtained from experiment.
$V_T^i$ is The volume at T and 1 atm of the amount of liquid inside the vessel at T and P after being corrected for pressure expansion of the test vessel:

$$V_T^i = \frac{W_{T,P} - \Delta v_{T,P}^{cor} \cdot \rho_{T,P}}{\rho_T} \qquad (7)$$

$W_{T,P}$: is the weight of liquid at T and P.
$\Delta v_{T,P}^{cor}$: is the change in volume of vessel at T and elevated pressure.
$\rho_{T,P}$: is the density of liquid at T and P.

$$\rho_{T,P} = \frac{W_{T,P}}{V_{T,P}} \qquad (8)$$

$V_{T,P}$ is the Volume of liquid at T and P.

$$V_{T,P} = v_{T,P} = v_T + \Delta v_{T,P}^{cor} \qquad (9)$$

$V_{T,P}$ is the Volume of vessel at T and P.

Substitute (6), (7), (8), (9) to (5) to obtain the empirical formula to calculate isothermal secant bulk modulus of a liquid (see 2.1.5 for derivation).

$$B_i = -\frac{\Delta P \cdot W_{T,P} \cdot v_T}{v_T \cdot (W_T - W_{T,P}) + W_T \cdot \Delta v_{T,P}^{cor}} \qquad (10)$$

with $\Delta P$, $W_T$, $W_{T,P}$ obtained from experiment $v_T$ and $\Delta v_{T,P}^{cor}$ obtained from calibration data. From experimental data, we can establish a P vs. $\Delta V/V$ curve and calculate the isothermal tangent bulk modulus. The relationship between $B_i$ and $B_t$ will be determined as a function of pressure and will be expressed as follows:

$$\frac{B_i}{B_t} = f(P)_T \qquad (11)$$

Figure 2:
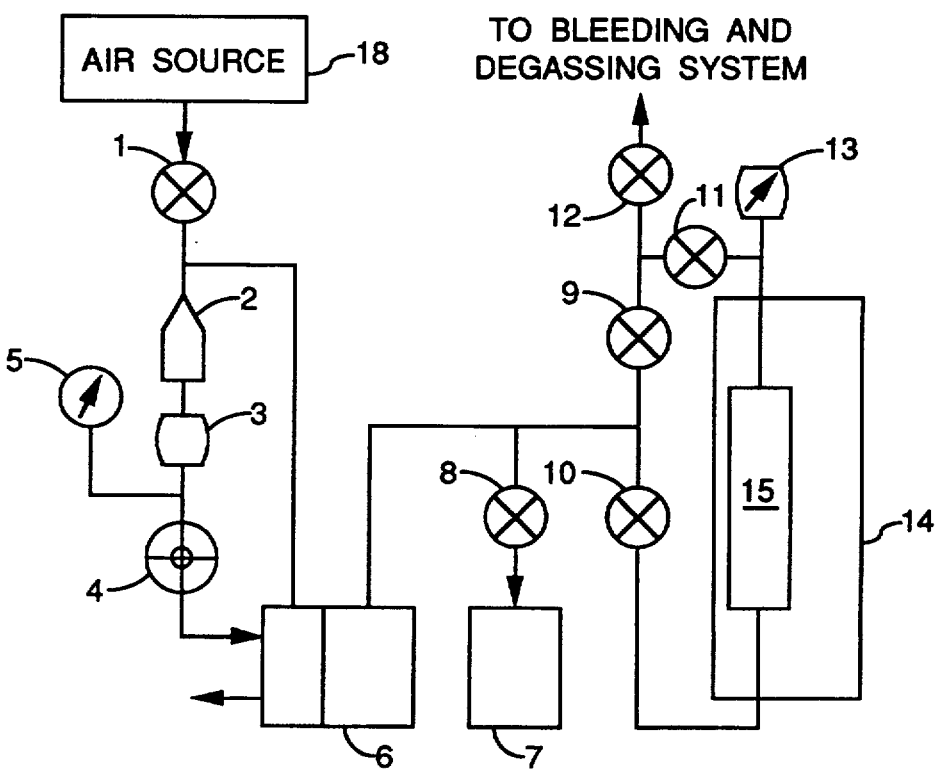
FIG. 2 is a schematic of the apparatus for the determination of viscosity at elevated pressure.

The calibration of Vessel Volume at Elevated Temperature and Atmospheric Pressure is determined by use of the apparatus shown in FIG. 2. This apparatus is the same as that of FIG. 1 except the valves 16 and 17 of FIG. 1 are not required.

The pressure vessel 15 (see FIG. 2) is filled with the test fluid and placed in a constant temperature bath until a thermal equilibrium is obtained. The valves are then closed and the fluid filled vessel cooled to ambient temperature.

The weight of empty vessel and of the fluid filled vessel together with density of the fluid at the test temperature and ambient pressure permit determination of the volume of the vessel at the test temperature:

$$v_T = \frac{W_T}{\rho_T} = \frac{W_{tot} - W_{vessel}}{\rho_T} \qquad (12)$$

The processes are repeated at different temperatures to obtain a $v_T(T)$ relationship which expresses vessel volume at any specified temperature at atmospheric pressure.

This calibration curve is used to determine final volume of liquid at T and P:

$$V_{T,P}^f = v_T \qquad (13)$$

To determine the volume change caused by internal pressure stress for the test vessel, it is necessary to calculate the increase in the inner diameter and the length of the vessel due to elevated pressure:
Increase in the inner radius of the vessel:

$$\Delta R_i = \frac{P_i R_i}{E} \left[ \frac{R_o^2(1 + \nu) + R_i(1 - 2\nu)}{R_o^2 - R_i^2 \gamma} \right] \qquad (14)$$

where:
$P_i$: Internal pressure in pressure vessel.
$R_i$: Inner radius of vessel.
$R_o$: Outer radius of vessel.
E: Young's modulus, psi.
$\gamma$: Poisson's ratio.
Increase in length of the vessel:

$$\Delta L = \frac{P_i L}{E} \left[ \frac{R_i^2(1 - 2\nu)}{R_o^2 - R_i^2} \right] \qquad (15)$$

where:
L: Length of vessel.
Increase in volume of the vessel:

$$\Delta V_{T,P}^{cor} = \pi[(L+\Delta L)(2R_i \Delta R_i + \Delta R_i^2) + R_i^2 \Delta L] \qquad (16)$$

Sample Calculation:
With pressure vessel CC4.55SS20 (SS316)
$R_i = 0.22$ in
$R_o = 0.375$ in
$P_i = 10,000$ psi
$L = 18.5$ in
$E = 27.94 \times 10^6$ psi (at T=70° F.)
$\rho = 0.27$
Substitute these values into (14) and (15), we get:
$\Delta R_i = 1.88 \times 10^{-4}$ in
$\Delta L = 1.75 \times 10^{-3}$ in
Thus:

$$\begin{aligned}\Delta v_{T,P}^{cor} &= \pi[(18.5 + 1.75 \times 10^{-3})2 \times .22 \times 1.88 \times 10^{-4} + \\ &\quad (1.88 \times 10^{-4})^2) + .22^2 \times 1.75 \times 10^{-3}] \\ &= 5.075 \times 10^{-3} \text{ in}^3 \\ &= 83.2 \,\mu l\end{aligned}$$

Repeat different elevated temperatures and pressures and make a graph of volume corrections for pressure at various temperatures.

The Empirical Formula to Calculate Isothermal Secant Bulk Modulus is:

$$B_i = -V_T^j \frac{\Delta P}{\Delta V_T} \quad (1)$$

or $$B_i = -\frac{\Delta P}{\frac{V_{T,P}^f - V_T^j}{V_T^j}} = -\frac{\Delta P}{\frac{V_{T,P}^f}{V_T^j} - 1} \quad (1a)$$

Substitute $V_{T,P}^f$ from (6) and $V_T^j$ from (7) to (1a), so that:

$$B_i = -\frac{\Delta P}{\frac{\frac{W_T}{\rho_T}}{\frac{W_{T,P} - \Delta v_{T,P}^{cor} \rho_{T,P}}{\rho_T}} - 1} \quad (1b)$$

Substitute $\rho_{T,P}$ from (8) and $V_{T,P}$ from (9) to (1b), so that:

$$B_i = -\frac{\Delta P}{\frac{W_T}{W_{T,P}\left[1 - \frac{\Delta v_{T,P}^{cor} W_{T,P}}{v_T + \Delta v_{T,P}^{cor}}\right]} - 1} \quad (1c)$$

$$B_i = -\frac{\Delta P}{\frac{W_T}{W_{T,P}\left[1 - \frac{\Delta v_{T,P}^{cor}}{v_T + \Delta v_{T,P}^{cor}}\right]} - 1} \quad (1d)$$

$$B_i = -\frac{\Delta P}{\frac{W_T}{W_{T,P}\left[\frac{v_T + \Delta v_{T,P}^{cor} - \Delta v_{T,P}^{cor}}{v_T + \Delta v_{T,P}^{cor}}\right]} - 1} \quad (1e)$$

$$B_i = -\frac{\Delta P}{\frac{W_T[v_T + \Delta v_{T,P}^{cor}]}{W_{T,P} v_T} - 1} \quad (1f)$$

$$B_i = -\frac{\Delta P[W_{T,P} v_T]}{W_T v_T + W_T \Delta v_{T,P}^{cor} - W_{T,P} v_T} \quad (1g)$$

$$B_i = -\frac{\Delta P W_{T,P} v_T}{v_T[W_T - W_{T,P}] + W_T \Delta v_{T,P}^{cor}} \quad (10)$$

Since $W_T < W_{T,P}$, $B_i > 0$.

This is the empirical formula to calculate isothermal secant bulk modulus.

The calculation of Isothermal Bulk Modulus (Tangent) is as follows:

$$B_T = V \frac{\partial p}{\partial v_T} = \frac{\partial p}{\partial \ln v_T} \quad (1)$$

for psi units of B, p is measured in psi and units of v cancel.

Isothermal secant bulk modulus $$B_s = \frac{P - P_o}{V_o - V} V_o \quad (2)$$

where:
$B_s$ = isothermal secant bulk modulus in psi $P_o$ = atmospheric pressure in psi
$P$ = measurement pressure in psi
$V_o$ = specific volume at $P_o$, cm$^3$
$V$ = specific volume at P, cm$^3$ $$V = \frac{1}{d_p}$$

where
$d_p$ = density at P $$V_o = \frac{1}{d_o}$$

where
$d_o$ = density at $P_o$

Determine density empirically as f(p) and derive a polynomial so that $$d = a + bp + cp^2 + dp^3 \quad (3)$$

or $$v = a' + b'p + c'p^2 + d'p^3 \quad (4)$$

This polynomial is then used to solve (1) or (2) for isothermal tangent or secant bulk modulus. The program provides for English as well as metric units.

The apparatus previously described for the determination of bulk modulus and density at various pressures and temperatures may readily be modified for the determination of viscosity under similar conditions of temperature and pressure. The modification, shown schematically in FIG. 2, consists simply of the substitution of a high pressure viscosity-temperature piston sensor for the pressure vessel 15. Sensors of the required type are readily obtainable. These may be employed for the direct determination of viscosity at elevated pressure provided the necessary corrections for the variation of sensor calibration with pressure are made. The corrections are as follows:

Where:
P = internal differential pressure, psi.
a = internal diameter of sensor shell = 0.314 inch
b = outer diameter of sensor shell = 0.383 inch
F/A = Stress = Force/unit area in wall of shell, psig.
S = Strain in shell.
d = incremental increase in inner diameter of shell as a result of strain, thousandths of an inch.
ACQ = acquisition coefficient of sensor = stroke seconds/viscosity in cp.
ANN = annulus = ID of shell minus piston OD, thousandths of an inch.
Y = Youngs modulus for Inconel = 31,000,000 psi.

The following relationships prevail:
F/A = pa/(b−a)
and $$S = F/AY = pa/(b-a)y \quad (1)$$

since $$d = aS = apa/(b-a)y \quad (2)$$

Then $$d = 0.0000461\,p \quad (3)$$

From a linear regression of data on the acquisition coefficient vs. annulus size, the following relationship has been developed:

$$\log (ACQ) = 1.8.754 - 2.8749 \log (ANN) \quad (4)$$

or $$K = ACQ_o/ACQ_1 = (ANN_1/ANN_o)\ 2.875 \quad (5)$$

where K = a correction factor for the distortion of the sensor shell.

$ACQ_o/ACQ_1 = $ Ratio of acquisition coefficient at zero pressure to acquisition coefficient at pressure. (6)

and $ANN_o/ANN_1 = (ANN_o + d)/ANN_o$ (7)
$= $ Ratio of annulus at pressure to annulus at zero differential pressure.

By substitution of the value of d from above $$K = ((ANN + 0.0000461p)/ANN\ 2.875 \quad (8)$$

where ANN is the diametrical annulus in mils and p is the pressure in psi, and K is the factor by which observed viscosities at elevated pressure must be multiplied to obtain correct viscosities.

By use of the pressure system as shown in FIG. 2, the piston type pressure viscosity—temperature sensor and the correction procedure described above, viscosities in centipoises (cp) may be determined over a wide range of temperatures and pressures. By combination of these data with pressure-density data obtained concurrently with the determination of bulk modulus, viscosities may also be determined by kinematic viscosity (i.e., cs).

Secant and tangent bulk modulus and density data and pressure viscosity data were obtained for a number of samples. The data for each sample are comingled because the pressure density values derived for bulk modulus measurements are required for the conversion of absolute viscosity (cp) to kinematic viscosity (cs).

The system described herein permits the determination of secant bulk modulus, isothermal tangent bulk modulus, density and viscosity as a function of pressure and temperature. The method has the advantage of relative simplicity; economy in that many components required for the determination of bulk modulus and density are interchangeable with those required for the determination of viscosity; safety because all pressures are hydraulic and no pneumatics are involved; and physical, relevance to hydraulic systems in which liquids function in a gas free, or near gas free environment.

Clearly, many modifications and variations of the present invention are possible in light of the above teachings and it is therefore understood, that within the inventive scope of the inventive concept, the invention may be practiced otherwise than specifically claimed.

The data which were obtained are contained in FIGS. 3 through 20 and in Tables 1 through 54 appended hereto and made a part hereof.

What is claimed is:

1. In a system for measuring isothermal secant bulk modulus $B_i$ of a liquid in a vessel on a pressure-volume-temperature relationship at a constant volume corrected for changes in vessel volume due to elevated pressure and temperature, a method comprising the steps of:
entirely filling said vessel with said liquid;
determining the volume $V_{T,P}^f$, where $V_{T,P}^f$ is the volume of liquid at temperature T;
determining the volume $V_T^i$ of the vessel at temperature T and 1 atmosphere; and $$\text{solve the equation } B_i = -\frac{\Delta P}{\frac{V_{T,P}^f - V_T^i}{V_T^i}}$$

where $\Delta P$ is equal to the difference in pressure P between 1 atmosphere and a specified pressure.

2. The method of claim 1, and
calibrating the volume of the vessel at various pressures and temperatures from atmospheric pressure and ambient temperature to various elevated temperatures and pressures to determine the final volume $V_{T,P}^f$, and establishing a calibration curve.

3. The method of claim 2, and an additional step of degassing said vessel prior to calibrating.

4. In a system for measuring isothermal secant bulk modulus $B_i$ of a liquid in a vessel on a pressure-volume-temperature relationship at a constant volume corrected for changes in vessel volume due to elevated pressure and temperature, where isothermal secant bulk modulus is defined as $$B_i = \frac{\Delta P}{\frac{V_{T,P}^f - V_T^i}{V_T^i}}$$

a method comprising the steps of:
entirely filling said vessel with said liquid;
degassing said vessel to remove any residual gas from said vessel;
determining the volume $V_{T,P}^f$, where $V_{T,P}^f$ is the volume of liquid at temperature T:
determining the volume $V_T^i$ of the vessel at temperature T and 1 atmosphere; and $$\text{solve the equation } B_i = \frac{\Delta P}{\frac{V_{T,P}^f - V_T^i}{V_T^i}}$$

where $\Delta P$ is equal to the difference in pressure between 1 atmosphere and the specified pressure.

5. In a system for measuring the isothermal secant bulk modulus $B_i$ of a liquid in a vessel on a pressure-volume-temperature relationship at a constant volume corrected for changes in vessel volume due to elevated pressure and temperature, a method comprising the steps of:
entirely filling said vessel with said liquid;
calibrating the volume of the vessel at various pressures and temperatures from atmospheric pressure and ambient temperature to various elevated temperatures and pressures to determine data relative to the final volume $V_{T,P}^f$, at any given pressure and temperature, and using said data to establish a calibration curve;
determining the volume $V_T$ of the vessel at atmospheric pressure and temperature T;
determining the weight $W_T$ of the liquids at temperature T and 1 atmosphere;
determining the density $D_T$ of the liquid at temperature T and 1 atmosphere; determining the volume $V_T^l$ of the liquid at temperature T and 1 atmosphere;

determining the volume $V_T^i$ of the amount of liquid inside the vessel at temperature T and pressure P after correction for expansion of the vessel due to pressure, where:

$$V_T^i = \frac{W_{T,P} - \Delta v^{cor}_{T,P} \cdot D_{T,P}}{D_T}$$

where:

$W_{T,P}$ is the weight of the liquid at temperature T and pressure P;

$\Delta v_{T,P}^{cor}$ is the change in volume of the vessel at temperature T and elevated pressure P;

$D_{T,P}$ is the density of the liquid at T and P and is equal to $W_{T,P}/v_{T,P} = v_T + v_{T,P}^{cor}$ and solving the equation $$B_i = -\frac{\Delta P \cdot W_{T,P} \cdot v_T}{v_T \cdot (W_T - W_{TP}) + W_T \cdot \Delta v_{T,P}^{cor}}.$$

* * * * *